US00PP24057P3

(12) United States Plant Patent

Deng et al.

(10) Patent No.: US PP24,057 P3

(45) Date of Patent: Dec. 3, 2013

(54) *LANTANA CAMARA* PLANT NAMED 'UF-T3'

(50) Latin Name: ***Lantana camara* L.**
Varietal Denomination: UF-T3

(75) Inventors: Zhanao Deng, Riverview, FL (US); David M. Czarnecki, II, Plano, TX (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 71 days.

(21) Appl. No.: 13/385,208

(22) Filed: Feb. 7, 2012

(65) Prior Publication Data

US 2013/0205457 P1 Aug. 8, 2013

(51) Int. Cl.
*A01H 5/00* (2006.01)

(52) U.S. Cl.
USPC ..... Plt./227

(58) Field of Classification Search
USPC ..... Plt./227
See application file for complete search history.

(56) References Cited

U.S. PATENT DOCUMENTS

PP14,569 P2 3/2004 Kearley et al.

OTHER PUBLICATIONS

Czarnecki et al., "Assessment of ploidy levels, pollen viability, and seed production of *Lantana camara* cultivars and breeding lines," abstract, *HortScience*, 43:1195-1196, 2008.

*Primary Examiner* — Annette Para
(74) *Attorney, Agent, or Firm* — Dentons US LLP

(57) ABSTRACT

A new and distinct cultivar of *Lantana camara* plant named 'UF-T3', characterized by its moderate vigor, mounding growth habit, free flowering, bright yellow/orange flower color, little fruiting, high level of female sterility, high level of male sterility, and lack of hybridization with *Lantana depressa*, is disclosed.

2 Drawing Sheets

Latin name of the genus and species of the plant claimed: *Lantana camara* L. (*Lantana strigocamara* R. W. Sanders).

Variety denomination: 'UF-T3'.

BACKGROUND OF THE INVENTION

The present invention relates to a new and distinct cultivar of *Lantana*, botanically known as *Lantana camara*, and hereinafter referred to by the name 'UF-T3'.

*Lantana camara* is a member of Verbenaceae. Plants of this species attract numerous species of butterflies, tolerate harsh environmental conditions, have low maintenance requirements, and are easy to grow, making *L. camara* highly desirable for use in containers, hanging baskets, and landscapes. Commercial production of *L. camara* is widespread in the nursery industry, especially in the southern United States. However, this species has escaped cultivation through seed dispersal and has hybridized (as pollen donors) with *Lantana depressa*, a rare species native to Florida, resulting in its classification as a Category I invasive species for South and Central Florida. Very few of the existing commercial *L. camara* cultivars are highly male- and female-sterile. Therefore, there has been a strong need for new sterile cultivars in *L. camara.*

'UF-T3' is a product of a planned breeding program at the University of Florida. The primary objective of the breeding program is to create new sterile *Lantana* cultivars with attractive plant growth habits (mounding, semi-mounding, to spreading), freely-flowering, and attractive flower coloration.

The new *Lantana* originates from a planned cross between 'Dallas Red' (unpatented) and a proprietary breeding line LAOP-9. 'Dallas Red' was selected as the female parent for its tetraploidy level, bright red flower color, and lack of production of unreduced female gametes. Breeding line LAOP-9 was selected out of a population of progeny from open pollinated 'Lola' (unpatented) in Wimauma, Fla. It was used as the male parent in the stated cross for its diploidy level, compact growth habit, and lack of production of unreduced female gametes. The stated cross was made in April 2007 in Wimauma, Fla. 'UF-T3' was discovered and selected in Wimauma, Fla. in October 2008 as one flowering plant within the progeny of the stated cross.

Asexual propagation of the new *Lantana* by vegetative cuttings in a controlled environment in Wimauma, Fla. since 2008 has shown that the unique features of this new *Lantana* are stable and reproduce true to type in successive generations.

BRIEF SUMMARY OF THE INVENTION

The cultivar 'UF-T3' has not been observed under all possible environmental conditions. The phenotype may vary somewhat with variations in environment and cultural practices such as temperature and light intensity without any change in genotype.

The following traits have been repeatedly observed and are determined to be the unique characteristics of 'UF-T3'. These characteristics in combination distinguish 'UF-T3' as a new and distinct cultivar of *Lantana:* 1) Moderate plant vigor; 2) Mounding and outwardly spreading growth habit; 3) Dense dark-green-colored leaves; 4) Freely flowering habit; 5) Yellow and orange-colored flowers that are held above and beyond the foliage; 6) Little fruiting and no or few berries; 7) High level of female sterility; 8) High level of male sterility; and 9) Little hybridization potential with *Lantana depressa.*

Plants of the new cultivar differ from plants of the female parent, the cultivar Dallas Red, in the following characteristics: 1) Plants of the new cultivar are triploids, while plants of 'Dallas Red' are tetraploids; 2) Plants of the new cultivar are mounding and outwardly spreading, while plants of 'Dallas Red' are more upright and erratic; 3) Flowers of the new cultivar are yellow-colored when initially open and turn orange when matured, while flowers of 'Dallas Red' are red-colored; 4) Plants of the new cultivar produce no or few fruit and are highly female-sterile, while plants of 'Dallas Red' are female-fertile and produce more fruit; and 5) Plants of the new cultivar have low pollen stainability or viability, while plants of 'Dallas Red' have much higher pollen stainability or viability.

Plants of the new cultivar differ from plants of the male parent, the breeding line LAOP-9, in the following characteristics: 1) Plants of the new cultivar are triploids, while plants of LAOP-9 are diploids; 2) Plants of the new cultivar are mounding and outwardly spreading, while plants of LAOP-9 are more upright; 3) Flowers of the new cultivar are yellow-colored when initially open and turn orange when matured, while flowers of LAOP-9 are yellow-colored; 4) Plants of the new cultivar produce no or few fruit and are highly female-sterile, while plants of LAOP-9 are female-fertile and produce more fruit; and 5) Plants of the new cultivar have low pollen stainability or viability, while plants of LAOP-9 have much higher pollen stainability or viability.

BRIEF DESCRIPTION OF THE DRAWINGS

The accompanying photographs illustrate the overall appearance of the new *Lantana* cultivar, as nearly as true as it is reasonably possible to obtain in colored reproductions of this type. Colors in the photographs may differ slightly from the color values cited in the detailed botanical description, which accurately describe the colors of the new *Lantana* cultivar.

DETAILED BOTANICAL DESCRIPTION

Figure 1:
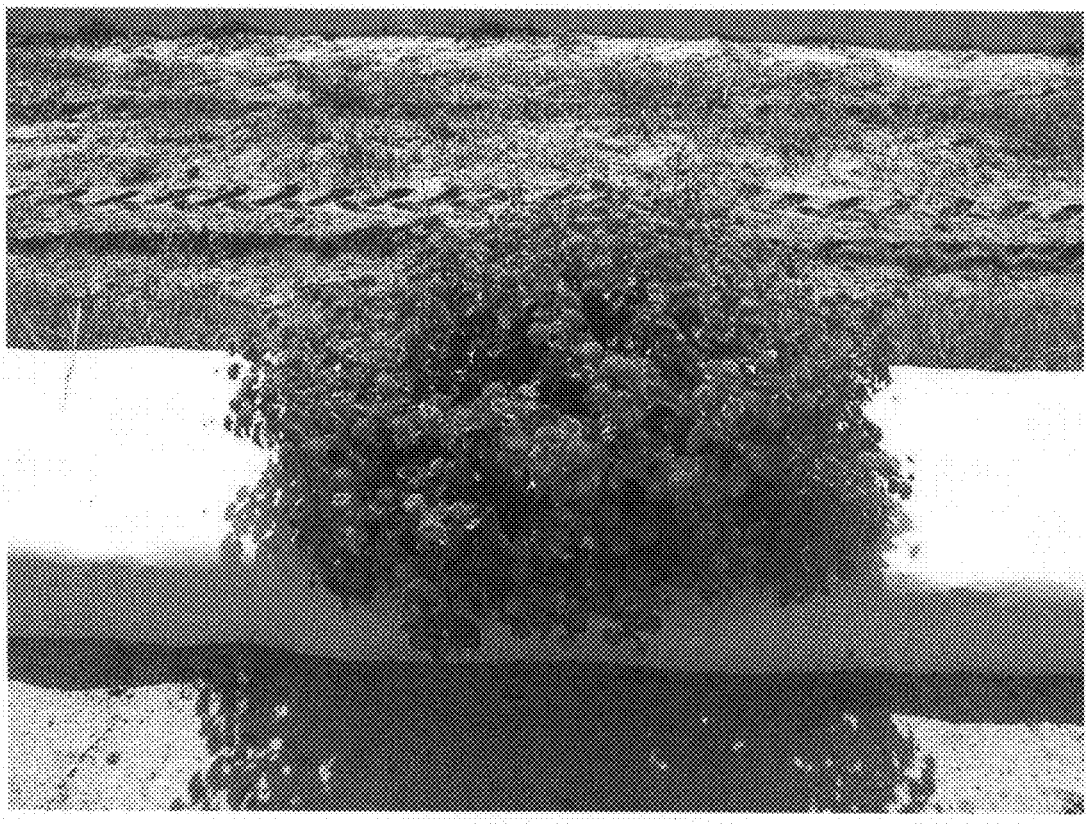
FIG. 1. Side perspective view of a typical flowering plant of 'UF-T3' grown in a ground bed in full sun. A single plant of 'UF-T3' *Lantana* propagated by cutting, grown in a soilless mix for 50 days, and grown outdoors in the ground bed for 70 days (photo taken at the Plant Science Unit in Citra, Fla. on Jul. 29, 2009).
Figure 2:
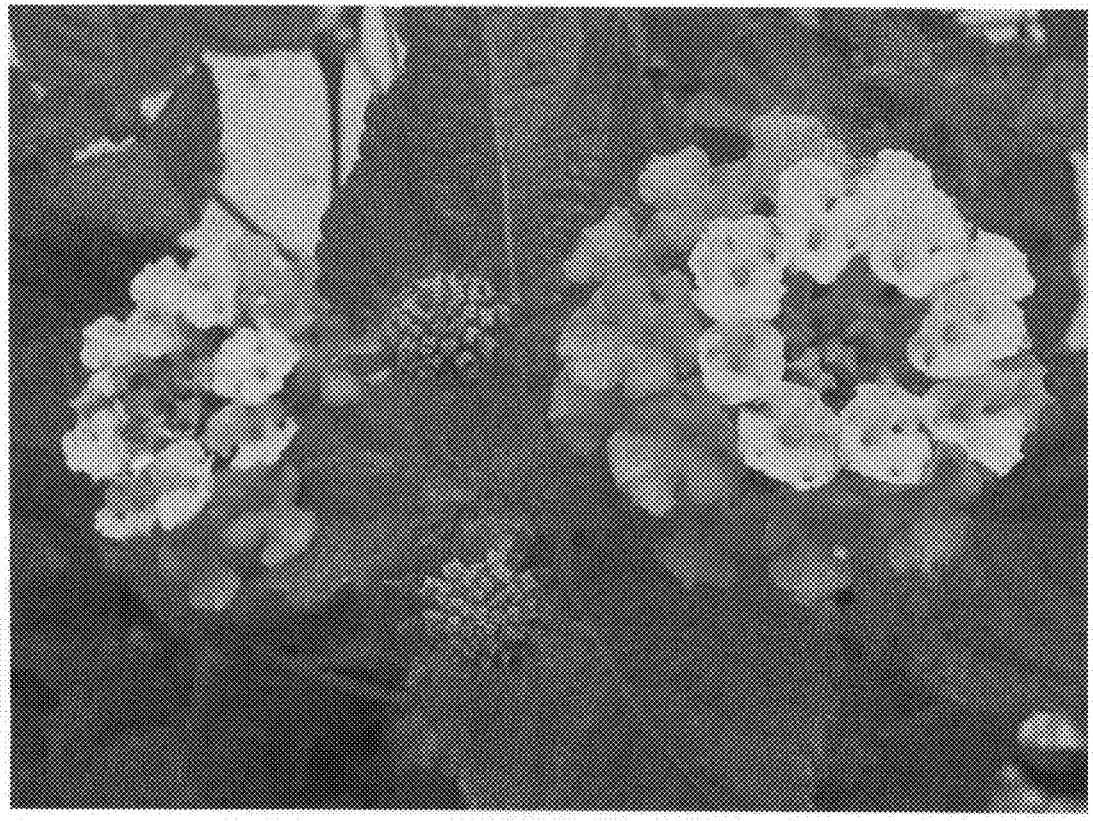
FIG. 2. Close-up view of typical inflorescences of 'UF-T3'. Inflorescences of 'UF-T3' lantana plants propagated by cutting and grown outdoors in full sun ground bed (photo taken at the University of Florida Gulf Coast Research and Education Center in Wimauma, Fla. on Sep. 20, 2011).

In the phenotypic description, color references are made to The Royal Horticultural Society Colour Chart (1986 Edition) except where general terms of ordinary dictionary significance are used. Plants used for the description were grown in the summer of 2011 in Wimauma, Fla. for 3 months from when terminal cuttings were made. Plants were planted in a 10.2-cm container and only trimmed minimally as needed at this time. Plants were grown outdoors for 3 weeks in early September in Wimauma, Fla. before flower color descriptions was done. During the production of the plants in the polypropylene-covered shadehouse, temperatures ranged from about 20.5° C. to about 36.1° C.

Phenotypic Description of *Lantana camara* L. (Variety 'UF-T3').

Propagation:

*Type of cutting*.—Terminal cutting.

*Time to initiate roots, summer*.—About 16 days at 27° C. winter: About 18 days at 27° C.

*Time to develop roots, summer*.—About 35 days at 24° C. winter: About 38 days at 24° C.

Roots:

*Description*.—Fine, fibrous.

*Color*.—Close to white (RHD 155B) initially then becoming closer to greyed-yellow (RHS 161D) with development.

*Rooting habit*.—Freely branching.

Plant:

*Description*.—Form: Flowering subshrub; upright and outwardly spreading plant habit: mounded plant form; freely branching: two lateral branches potentially forming at every node; pinching enhances lateral branch development.

*Plant height*.—About 24 cm.

*Plant diameter*.—About 33 cm.×25 cm.

*Lateral branch*.—Length: About 22 cm. Diameter: About 3.3 mm. Internode length: About 4.9 cm. Strength: Strong, but flexible. Texture: Rough, pubescent. Color: Young: Close to yellow-green (RHS 144A). Woody: Close to greyed-brown (RHS 199A to brown RHS 200D).

Stem:

*Quantity of main branches per plant*.—3-4.

*Quantity of leaves per branch*.—5-12.

*Length of stem*.—19-24 cm.

*Diameter*.—5.7 cm.

*Length of internodes*.—1.5-7 cm.

*Texture*.—Pilose, and a few glandular hairs.

*Color of stem*.—Young: Close to yellow-green (RHS 144A). Woody: Close to greyed-brown (RHS 199A to brown RHS 200D).

Foliage:

*Arrangement*.—Opposite; simple.

*Length*.—About 8 cm.

*Width*.—About 6 cm.

*Shape*.—Ovate. Apex: Acute. Base: Obtuse with truncate tendencies.

*Margin*.—serrate.

*Texture, upper and lower surfaces*.—Leathery, rough, coarse; pubescent.

*Luster*.—Upper surface: Slightly glossy. Lower surface: Dull.

*Venation pattern*.—Pinnate, arcuate.

*Color*.—Developing and fully expanded foliage. Upper surface: Close to yellow-green (RHS 147A). Lower surface: Close to yellow-green (RHS 147B).

*Color*.—Venation. Upper surface: Close to yellow (RHS 145B). Lower surface: Close to yellow-green (RHS 145C).

*Petiole length*.—About 1.7 mm.

*Petiole diameter*.—About 2.3 mm.

*Petiole texture, both surfaces*.—Slightly pubescent.

*Petiole color, upper surface*.—Close to green (RHS 143C). lower surface: Close to green (RHS 143B).

Inflorescences and flower:

*Flower type*.—Small salverform flowers arranged in axillary umbels; flowers face mostly upward or outward.

*Flowering habit*.—Very freely flowering, with potentially two inflorescences per node; typically about 32 flowers per umbel; Flowers self-cleaning; flowering continuous and consistent spring until frost in the autumn.

*Flower longevity on the plant*.—About one week.

*Fragrance*.—Faint, pleasant.

*Inflorescence diameter*.—About 3.6 cm.

*Inflorescence height*.—About 2.6 cm.

*Number of flowers per inflorescence*.—About 30-34.

*Quantity of inflorescences per plant*.—About 10-16.

*Flower appearance*.—Flared trumpet, corolla fused, four-parted; flowers roughly rectangular in shape.

*Flower diameter*.—About 1 cm×1 cm.

*Flower buds (before showing color)*.—Diameter: About 9.1 mm. Shape: Roughly spherical to ovoid. Color: Close to green (RHS 143A).

*Bract*.—Length: 5.5 mm. Diameter: 1 mm. Color: yellow-green (RHS 145A) with a yellow-green (RHS 147A) apex. Texture: Outer surface: Hirsute. Inner surface: Glandular hairs on the inner surface.

*Corolla*.—Arrangement/appearance: Single whorl of four petals, fused into flared trumpet. Tube length: 1.1 cm. Throat and tube texture: Outer surface: Pubescent. Inner surface: Papillose. Color tube color: (matured) Outer surface: Close to orange red (RHS 35D). Inner surface: throat: Close to yellow-orange (RHS 23B). tube: Close to yellow-orange (RHS 18D).

*Petal*.—Length from throat: Upper and lower petals: About 5 mm. Lateral petals: About 4 mm. Width: Upper and lower petals: About 6.5 mm. Lateral petals: About 3.5 mm. Shape: Spatulate to somewhat rectangular. Apex Rounded. Margin: Entire. Degree of lobation: Moderate.

*Petal lobe texture, upper and lower surfaces*.—Smooth, velvety. Color: Petal lobes, when opening, (immature): Upper surface: Close to yellow-orange (RHS 17A) and changes close to yellow-orange (RHS 23A). Eye color: Close to orange (RHS 28B). Petal lobes, when opening, (immature). lower surface: Close to yellow (RHS 13A) and other surfaces close to orange-red (RHS 30D). Petal lobes, fully opened, (matured). upper surface: Close to orange (RHS 28A). Petal lobes, fully opened, (matured). Lower surface: Close to orange (RHS 25D). Throat: Close to orange (RHS 25D). Tube: Close to orange-red (RHS 35D).

*Calyx*.—Number of sepals: One sepal per flower. Length: About 4 mm. Width: About 1 mm. Shape: Lanceolate. Apex: Acute. Base: Truncate. Texture: upper surface: Pubescent. lower surface (inside) Pubescent. Color: apex: Close to yellow-green (RHS 144A). base: Close to yellow-green (RHS 145B).

*Peduncles*.—Length: About 3 cm. Diameter: About 1 mm. Angle: About 45 degree from the stem. Strength: Flexible, but strong. Texture: Pubescent. Color: Close to yellow-green (RHS 144A).

*Pedicels*.—Not observed, flowers not stalked.

Reproductive organs:

*Stamens*.—Quantity/arrangement: Four per flower, adnate to floral tube. Length of filament: About 2 mm. Color of filament: Close to yellow (RHS 9C).

*Anther*.—Shape: Oblong. Length: Less than 1 mm. Color: Close to yellow (RHS 9B).

*Pistils*.—Quantity: One per flower. Length: About 4 mm.

*Stigma shape*.—Oblong. Color: Close to yellow-green (RHS 144C).

*Ovary*.—Color: Close to yellow-green (RHS 144B).

*Pollen*.—Amount: none observed.

ASSESSMENT OF FEMALE FERTILITY

Four experiments were conducted simultaneously at the Indian River Research and Education Center (IRREC) in Ft. Pierce, Fla. (southeast Florida, USDA hardiness zone 10, and AHS heat zone 9-10), at the GCREC in Balm, Fla. (southwest Florida, USDA hardiness zone 9A, and AHS heat zone 10), at the Plant Science Research and Education Unit (PSREU) in Citra, Fla. (northern Florida, USDA hardiness zone 8B, and AHS heat zone 10), and at the North Florida Research and Education Center (NFREC) in Quincy, Fla. (northern Florida, USDA hardiness zone 8B, and AHS heat zone 9). The four experiment sites are located in three different hardiness zones (10, 9A, and 8B) and two different heat zones (10 and 9) (American Horticultural Society, 1998; National Gardening Association, 2011). The experimental design used in Ft. Pierce and Balm was a randomized complete block with three blocks. The distance between field blocks were at least 50 feet. Each plot within the block at these two sites consisted of two plants for each cultivar and one *L. depressa* plant (mixed planting of triploids and native *Lantana*). The spacing between plants within each plot was 6 feet. The same experimental design and the same number of blocks were used in Quincy and Citra, except that *L. depressa* plants were not installed between triploid plants (pure planting of triploid plants). *L. depressa* does not occur naturally in north Florida. At each experimental site, 'Pink Caprice' was included as a control. It is commercially produced and very prolific in fruit (and seed) production. 'Pink Caprice' was planted at least 150 feet away from 'UF-T3'.

Every four weeks beginning on late July 2009 until mid-December 2009, 20 peduncles (flower or fruit clusters) were harvested randomly from each of the plants grown at the four experimental sites (refer to the above) and berries on each peduncle were counted. A total of six harvests were made for each plant at each experimental site. Thus 120 peduncles were examined for each *Lantana* cultivar in each experimental plot during a given harvest and 2,880 peduncles were examined across the four experimental sites through six harvests (20 peduncles per plant×2 plants within a block×3 blocks×4 sites×6 harvests) for each cultivar. An analysis of variance was conducted using the general linear model provided in SAS (PROC GLM; SAS Institute 2011) to compare the fruit production of 'UF-T3' with that of 'Pink Caprice'.

'Pink Caprice' produced many more berries. Each peduncle of 'Pink Caprice' bore an average of 1.143 to 22.838 berries, with an overall average of 10.451 across the four sites and six harvests. The number of berries per peduncle on 'Pink Caprice' grown in Balm and Ft. Pierce ranged from 1.143 to 12.416, averaged to 6.783, while the number of berries per peduncle on plants grown in Quincy and Citra was 7.150 to 22.838, averaged to 14.118, more than 1-fold greater.

The number of berries 'UF-T3' produced per peduncle ranged from 0 to 0.074 and averaged to 0.019 across four experimental sites and over 6 months (Table 1). This level of fruit production represents greater than 99% reduction from the fruit production capacity of 'Pink Caprice's'. 'UF-T3' showed similarly low levels of fruit production regardless of whether they were planted purely (without *L. depressa* in Quincy and Citra) or interplanted with *L. depressa* (in Balm and Ft. Pierce).

Mature berries were collected from each plant in the above described experiments. Seeds were extracted, cleaned, and air-dried. Seeds were germinated in a 10.9-cm×10.9-cm transparent polystyrene germination boxes (Anchor Paper Company, St. Paul, Minn.) containing 2 sheets of germination paper (Anchor Paper Company) moistened with 15 mL of nanopure water. Germination boxes were placed in temperature and light-controlled chambers equipped with cool-white fluorescent lamps (Model 818; Precision Scientific, Winchester, Va.). The germination condition was 12 hours light at 25° C. (photosynthetic photon flux was 22 to 30 μmol $m^{-2}s^{-1}$ at shelf level) followed by 12 hours dark at 15° C. Germination of seeds was monitored every other day for a period of 60 days. An additional 5-10 mL of nanopure water was added to the germination boxes as needed. A seed was considered germinated when radicle emergence was 2.0 mm or greater. Seeds were removed once germination occurred to prevent inaccurate data collection.

'Pink Caprice' seeds germinated readily, with an average germination percentage of 63.3 (Table 2). The number of seeds collected from each experimental site (six plants) over 6 months for 'UF-T3' ranged from 0 to 13 (Table 2). The germination percentage of these seeds was between 15.4 and 50.0, averaged to 24.4 (Table 2).

Fruit (seed) production per peduncle and seed germination are the primary factors determining *Lantana's* female fertility (or sterility). These two characteristics are factored into a female fertility index (FFI) by multiplying fruit production per peduncle and seed germination. The FFI for 'UF-T3' was 0.005 (Table 2), less than 0.1% of the 'Pink Caprice's' FFI (6.615), indicating an extremely high level of female sterility in 'UF-T3'.

TABLE 1

Fruit production of 'UF-T3' and 'Pink Caprice' grown outdoors in ground beds in full sun at four experimental sites in Quincy, Citra, Balm, and Ft. Pierce in Florida (2009).

| Cultivars | Expt. site[z] | Type of planting[y] | Fruit per peduncle (no.) at the following weeks post planting 12 | 16 |
|---|---|---|---|---|
| UF-T3 | Quincy | Pure | 0.008 d[x] | 0.000 d |
| | Citra | Pure | 0.025 d | 0.008 d |
| | Balm | Mixed | 0.000 d | 0.017 d |
| | Ft. Pierce | Mixed | 0.025 d | 0.033 d |
| Pink Caprice | Quincy | Pure | 7.150 b | 22.838 a |
| | Citra | Pure | 15.808 a | 10.867 b |
| | Balm | Mixed | 1.143 d | 10.683 b |
| | Ft. Pierce | Mixed | 5.067 c | 6.608 c |

| Cultivars | Expt. site[z] | Fruit per peduncle (no.) at the following weeks post planting 20 | 24 | 28 |
|---|---|---|---|---|
| UF-T3 | Quincy | 0.008 e | 0.000 d | 0.000 e |
| | Citra | 0.000 e | 0.000 d | 0.000 e |
| | Balm | 0.074 e | 0.033 d | 0.017 e |
| | Ft. Pierce | 0.025 e | 0.025 d | 0.042 e |
| Pink Caprice | Quincy | 20.825 a | 17.000 a | 11.138 b |
| | Citra | 16.092 b | 9.175 b | 12.783 a |
| | Balm | 12.415 c | 4.226 c | 8.883 c |
| | Ft. Pierce | 9.525 d | 8.000 b | 4.583 d |

TABLE 1-continued

Fruit production of 'UF-T3' and 'Pink Caprice' grown outdoors in ground beds in full sun at four experimental sites in Quincy, Citra, Balm, and Ft. Pierce in Florida (2009).

| Cultivars | Expt. site[z] | Fruit per peduncle (no.) at the following weeks post planting 32 | Average | Average across all sites over 20 weeks |
|---|---|---|---|---|
| UF-T3 | Quincy | 0.033 e | 0.008 d | 0.019 b |
| | Citra | 0.017 e | 0.008 d | |
| | Balm | 0.016 e | 0.026 d | |
| | Ft. Pierce | 0.033 e | 0.031 d | |
| Pink Caprice | Quincy | 11.275 b | 15.038 a | 10.451 a |
| | Citra | 14.467 a | 13.199 b | |
| | Balm | 7.532 c | 7.481 c | |
| | Ft. Pierce | 2.733 d | 6.086 c | |

[z]Plants were propagated by cuttings and grown in #1 contains before installed in the ground beds. Planting was completed in the week of 5 May 2009 for the sites Quincy (University of Florida North Florida Research and Education Center), Citra (University of Florida Plant Science Unit), Balm (University of Florida Gulf Coast Research and Education Center), and Ft. Pierce (University of Florida Indian River Research and Education Center).
[y]Pure = two triploid plants of the same cultivar per plot without *L. depressa* plants; "mixed" = one *L. depressa* plant was installed between the two triploid plants. The experimental design at each site was a randomized complete block with three replicates and two plants per plot.
[x]Mean of 120 peduncles (3 blocks or replicates, 2 plants per block, and 20 peduncles per plant). Means with the same letter within the column are not significantly different by the LSD procedure at $P \leq 0.05$.

TABLE 2

Final germination (%) of seeds and female fertility index of 'UF-T3' and 'Pink Caprice'.

| | Seeds in germination tests (no.) Quincy | Citra | Balm | Ft. Pierce | Germination (%)[z] Quincy | Citra |
|---|---|---|---|---|---|---|
| UF-T3 | —[w] | 2 | 13 | 12 | —[w] | 50.0 |
| Pink Caprice | 100 | 100 | 100 | 100 | 71.0 | 49.0 |

| | Germination (%)[z] Balm | Ft. Pierce | average | Average fruit per peduncle[y] | Female fertility index[x] |
|---|---|---|---|---|---|
| UF-T3 | 15.4 | 33.3 | 24.4 | 0.019 | 0.005 |
| Pink Caprice | 71.0 | 62.0 | 63.3 | 10.451 | 6.615 |

[z]Seeds were collected from plants grown at four sites (NFREC in Quincy, PSRU in Citra, GCREC in Balm, and IRREC in Ft. Pierce) and germinated for 60 days at the IRREC in 2009. Germination conditions were under 12 hr photoperiod, 25° C. (day) and 15° C. (night), in germination boxes placed in growth chambers. A maximum of 100 seeds were placed in a germination box. Analysis of variance was not conducted due to the limited seed numbers.
[y]Average fruit production per peduncle from Table 1.
[x]Female fertility index = average fruit production per peduncle × seed germination (%)/100.
[w]No seeds were produced and collected during the 32-week growing season for germination tests.

ASSESSMENT OF POLLEN STAINABILITY

Pollen stainability is a good indicator of *Lantana's* male fertility (or sterility) and hybridization potential with *Lantana depressa*. Three pollen staining experiments were conducted using fresh anthers collected from the plants grown in Wimauma, Fla. on 24 September and again on 16 Nov. 2009 and from the plants grown in Ft. Pierce on 6 Oct. 2009. In each staining experiment, three inflorescences were collected per plant and three to four anthers were isolated from each of the inflorescences, resulting in eight to 12 anthers from any given plant and 48 to 72 anthers for each lantana cultivar (two plants per replicate and three replicates in each location). Collected anthers were placed in ~100 μL of cotton blue solution (Eng Scientific, Inc. Product No. 6730, Clifton, N.J.) in a 1.5-mL Eppendorf tube and stained overnight at 65° C. Stained anthers were rinsed three times with deionized water, placed onto a microscope slide, squashed in a drop of 80% glycerol, and covered with a cover slip. Pollen grains were observed under 400× magnification on a BH-2 microscope (Olympus, Tokyo, Japan). Well developed, full and deeply stained pollen grains were counted as stainable, while non-stained, partially stained, or abnormally-shaped pollen grains were counted as non-stainable (aborted). The number of pollen grains examined for each *Lantana* cultivar in each staining experiment was between 1,752 and 5,141. An analysis of variance was conducted using the general linear model provided in SAS (PROC GLM; SAS Institute 2011) to compare the pollen stainability of 'UF-T3' and 'Pink Caprice'. The average pollen stainability of 'UF-T3' was 5.1% (Table 3). The average pollen stainability of 'Pink Caprice' was 65.6% (Table 3). These results indicate that the pollen stainability (or male fertility) of 'UF-T3' has been reduced by 92.2% from that of 'Pink Caprice'.

ASSESSMENT OF HYBRIDIZATION POTENTIAL WITH *Lantana depressa*

Two hand pollination experiments were performed in the greenhouse in Wimauma, Fla., one in fall 2009 and one in spring 2010, to assess the ability of 'UF-T3' to cause fruit set on *L. depressa* flowers. Stock plants were grown in #1 plastic containers filled with a commercial soilless mix amended with a controlled release fertilizer (Osmocote, 15N-3.9P-10K, 8-9 months release at 21° C.) at 7.12 $kg \cdot m^{-3}$. Temperatures inside the greenhouse ranged from a low of 16° C. at night to a high of 29° C. during day. No supplemental lighting was provided. Plants were drip-irrigated, twice a week as needed. Fresh anthers were collected from mature unopened flowers of 'UF-T3' and applied immediately to emasculated *L. depressa* flowers.

'UF-T3' effected 2.8% fruit set in the first hand-pollination experiment but no fruit set in the second pollination experiment. Two seeds were obtained but they did not germinate (Table 4). 'Pink Caprice' effected an average of 8.9% fruit set. Seeds from *L. depressa*×'Pink Caprice' had 65% germination. These results confirm the high level of pollen infertility in 'UF-T3' compared to 'Pink Caprice'.

TABLE 3

Pollen stainability of 'UF-T3' and 'Pink Caprice' grown outdoor in ground beds in full sun (2009).

| | Pollen grains examined (no.) | | | | Pollen stainability (%)[z] | | | |
|---|---|---|---|---|---|---|---|---|
| | Expt. 1[y] | Expt. 2[x] | Expt. 3[w] | Total | Expt. 1 | Expt. 2 | Expt. 3 | Overall average |
| UF-T3 | 5,141 | 3,752 | 4,025 | 12,918 | 6.5 b[v] | 6.4 b | 2.4 b | 5.1 b |
| Pink Caprice | 2,211 | 2,030 | 1,752 | 5,993 | 62.0 a | 65.1 a | 69.9 a | 65.6 a |

[z]Fresh anthers were stained in cotton blue overnight at 65 C. before they were examined under a microscope.
[y], [x]Anthers were collected on 24 Sep. 2009 and 16 Nov. 2009 from plants (3 blocks and 2 plants per block) at the University of Florida Gulf Coast Research and Education Center, Balm, FL.
[w]Anthers were collected on 6 Oct. 2009 from plants (3 blocks and 2 plants per block) at the University of Florida Indian River Research and Education Center, Ft. Pierce, FL.
[v]Means with the same letter within the column are not significantly different by the LSD procedure at $P \leq 0.05$.

TABLE 4

Hybridization potential of 'UF-T3' with *L. depressa* as compared to 'Pink Caprice'.

| | *L. depressa* flowers pollinated (no.) | | *L. depressa* fruit set (%) | | | Seed |
|---|---|---|---|---|---|---|
| | Fall 2009 | Spring 2010 | Fall 2009 | Spring 2010 | Average | germination (%) |
| UF-T3 | 64 | 114 | 2.8 | 0.0 | 1.4 | 0 |
| Pink Caprice | 305 | 93 | 1.6 | 16.1 | 8.9 | 10 |

What is claimed is:

1. A new and distinct cultivar of *Lantana camara* plant named 'UF-T3', as illustrated and described herein.

* * * * *